(12) United States Patent
Woodward et al.

(10) Patent No.: US 6,215,013 B1
(45) Date of Patent: Apr. 10, 2001

(54) PREPARATION OF PHOSPHONIC ACID DERIVATIVES

(75) Inventors: Gary Woodward, Worcester; Timothy Kevin Brierley, Cheshire; Ranbir Singh Padda, Oxon; John Christopher Harris, Worcester; Aidan Michael Hayes, Worcestershire, all of (GB)

(73) Assignee: Rhodia Consumer Specialties Limited, West Midlands (GB)

( * ) Notice: Subject to any disclaimer, the term of this patent is extended or adjusted under 35 U.S.C. 154(b) by 0 days.

(21) Appl. No.: 09/582,967

(22) PCT Filed: Dec. 24, 1998

(86) PCT No.: PCT/GB98/03911

§ 371 Date: Sep. 5, 2000

§ 102(e) Date: Sep. 5, 2000

(87) PCT Pub. No.: WO99/35151

PCT Pub. Date: Jul. 15, 1999

(30) Foreign Application Priority Data

Jan. 10, 1998 (GB) ................................... 9800452

(51) Int. Cl.$^7$ ................................. C07F 9/40; C07F 9/38
(52) U.S. Cl. ........................... 558/142; 558/87; 558/217; 562/8; 562/22
(58) Field of Search ................................ 558/142; 562/8, 562/22

(56) References Cited

U.S. PATENT DOCUMENTS 3,686,290 8/1972 Carroll .

FOREIGN PATENT DOCUMENTS 0 252 244    1/1988  (EP) .
WO 95 06052  3/1995  (WO) .

OTHER PUBLICATIONS

Blazer B.: "Ober 1–hydroxyalkan–1,1–diphosphonsauren", Zeitschrift Fur Anorganische Und Allgemeine Chemie., vol. 381, No. 3, 1971, pp. 247–259, XP002099293, Leipzig DD.

Collins A.J.: "Preparation, properties, and crystal structure of the cyclic compound formed by thermal dehydration of 1–hydroxyethylidenediphosphonic acid"; Journal of the Chemical Society Dalto Transactions., No. 9, 1974, pp. 960–964, XP002099294 Letchworth GB.

*Primary Examiner*—Michael G. Ambrose
(74) *Attorney, Agent, or Firm*—Frishauf, Holtz, Goodman, Langer & Chick, P.C.

(57) ABSTRACT

A method for the preparation of alkene phosphonic acids and salts thereof, such as VDPA (vinylidene diphosphonic acid) is disclosed. The products can be produced in a stable, substantially pure form and in high yield. The method includes the azeotropic removal of water from salts of α-hydroxy-alkane diphosphonic acid dimer or corresponding acids thereof, and the pyrolysis of the dehydrated reactant at a temperature of from 170° C. to 300° C. There may be included a step to convert anhydrides which have been formed during the pyrolysis. The method may include the use of heat transfer agents and/or bases, and may be carried out at elevated or reduced pressure.

30 Claims, No Drawings

PREPARATION OF PHOSPHONIC ACID DERIVATIVES

The present invention provides a novel method for the preparation of phosphonic acid derivatives, especially alkene diphosphonic acids e.g. vinylidene diphosphonic acid (VDPA) and salts thereof. Said phosphonic acids and salts are produced in a purer form than has hitherto been achieved and in a high yield.

VDPA exhibits greater chelancy than VPA. VDPA is known for use as a chelant for metals and for use in pharmaceutical applications. VDPA and VPA may be used in combination with each other according to the required properties of the mixture, depending upon the application in question. Because of its ability to polymerise, VDPA may be used as a copolymer with other polymerisable compounds.

VDPA is conventionally prepared from either methylene bis phosphonates, or from diphosphonic acid derivatives.

U.S. Pat. No. 3,686,290 describes the preparation of VDPA salts from the tetrasodium salt of 1-hydroxy, 1-ethylidene diphosphonic acid, at a pyrolysis temperature of from 300° C. to 500° C., preferably 350° C. to 425° C. However the product is typically obtained in low yields.

EP-0-252-244 describes the preparation of VDPA salts from the sodium salt of 1-(O-acyl)ethane-1,1-diphosphonic acid, at a temperature of between 200° C. to 250° C. However the product is typically obtained in a maximum yield of 75%.

The preparation of VDPA from bis phosphonates, using a two step procedure involving the base catalysed reaction of an ethylene bis(phosphonate)ester with paraformaldehyde followed by acid catalysed elimination of methanol and conversion to the free acid by reaction with bromotrimethylsilane is described in J. Org. Chem 1986, 51,3488–3490.

It has been found that alkene diphosphonic acids and their derivatives produced by this method typically exhibit a purity of less than 80 mol %, and were produced in low yield.

The multistage production of VDPA and its derivatives from methylene diphosphonate and bis(diethylamino) methane using temperatures of 170–180° C. is described by Prishchenko et al in *Zhurnal Obshchei Khimii*. Vol 61. No.4.p.1018. It has been found that this method produces low yields (58%), and products of low purity.

There are several disadvantages associated with the known methods of preparation of alkene diphosphonic acids, although not all disadvantages may be associated with each known method. Some require high dehydration temperatures, typically above 400° C., to produce the alkene diphosphonic acids. This is above the decomposition temperature of approximately 285° C. of tetra-sodium VDPA and hence products are obtained in a low yield and are of low purity due to the presence of high amounts of esters of the aforementioned acids. The methods of preparation of the prior art typically provide products of, for example, 50 mol % to 80 mol % purity. This may be unacceptably low for some uses, for example pharmaceutical applications. Furthermore due to the impure products typically obtained by said known methods of preparation longwinded and cumbersome purification methods are frequently required.

There is therefore a requirement to provide a method of preparation of alkene phosphonic acids, such as VDPA which produces the reaction product in a stable, purer form than has hitherto been possible, whilst being obtained in a high yield. Furthermore the method of preparation should preferably require the products to undergo minimal purification.

We have now discovered that alkene phosphonic acids e.g. VDPA may be prepared from the salts of α-hydroxy-alkane diphosphonic acid dimers or the corresponding acids thereof, by the dehydration of the reactant followed by the low temperature pyrolysis thereof. The dehydration and pyrolysis may be carried out in the presence of a heat transfer agent.

The alkene phosphonic acids prepared by the method of the invention are obtained in high yield and in a substantially pure form.

According to one embodiment, the present invention provides a method of preparation of alkene phosphonic acids or salts thereof of general formula (I):

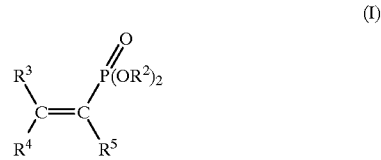

(I)

wherein each $R^2$ is independently H, an alkyl group, an alkali metal, an alkaline earth metal, or a nitrogen-containing group;

$R^3$ and $R^4$ are independently H, or an alkyl group; and $R^5$ is H, an alkyl group or

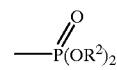

wherein said method comprises the steps:
(a) the azeotropic removal of water from the reactant of general formula (II)

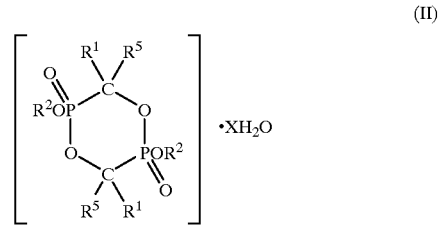

(II)

wherein $R^1$ is $CHR^3R^4$;
$R^2$, $R^3$, $R^4$ and $R^5$ are as hereinabove defined; and
X is a number between 0 and 20,
(b) the pyrolysis of the dehydrated reactant (II) at a temperature of from 170° C. to 300° C., and
(c) optionally, conversion of any anhydrides formed during stage (b) to the corresponding acid or salt having the general formula (I).

According to a second embodiment, the present invention provides a method for the preparation of alkene phosphonic acids or salts thereof of general formula (I) as hereinabove defined, wherein
(a) said azeotropic removal of water from said reactant (II) is carried out by dehydrating a reactant of general formula (II) in the presence of at least one inert liquid heat transfer agent which exhibits effective azeotropic properties with water and which is liquid at the reaction temperature; and
(b) said pyrolysis of dehydrated reactant (II) is carried out by adding at least one inert heat transfer agent which is liquid at the reaction temperature to the reaction mixture from (a), and the reaction mixture is maintained at 170° C. to 300° C. until pyrolysis of the dehydrated reactant (II) is complete According to a third embodiment, the present invention provides a method of preparation of the alkene phosphonic acids or salts thereof of general formula (I) as defined hereinabove, wherein pyrolysis of the dehydrated reactant (II) at a temperature of from 170° C. to 300° C. is in the presence of at least one base, and optionally at least one inert heat transfer agent.

Reactants and Products

The alkene phosphonic acids are produced from a cyclic reactant of general formula (II) as given hereinabove, which may be present either as a salt or as the acid. Suitable salts of the acid include amongst others the alkali metal, alkaline earth metal, or nitrogen-containing salts. The alkyl groups $R^2$, $R^3$ and $R^5$ are preferably each $C_1$–$C_6$ alkyl groups. The or each nitrogen-containing group $R^2$ is preferably an amine salt. Particularly preferred as a reactant is the hexa-sodium salt of ADPA dimer [Formula (II) wherein $R^1$ is $CH_3$,

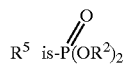

and $R^2$ is Na]

Said reactant (II) may be produced in situ without being isolated and said reactant may be subsequently converted to a compound having the general formula (I) i.e. by means of a multistage preparation incorporating the process of the present invention. An example of such a multistage reaction is the conversion of phosphorous acid and acetic anhydride to the sodium salt of ADPA dimer, followed by the conversion of said dimer to VDPA by the process of the present invention. Alternatively the process of the present invention may be used to convert the isolated cyclic reactant e.g. ADPA dimer or the sodium salt thereof, to the alkene phosphonic acid (I).

The reactant may be added to the reaction vessel as a solid or as a solution e.g. an aqueous solution.

The present invention provides a particularly advantageous method for the preparation of alkene diphosphonic acids of general formula (I).

Reaction Conditions

Any one or more of steps (a), (b) and (c) of the method of the invention may be carried out under reduced pressure. Alternatively any one or more of steps (a), (b) and (c) of the method may, if required, be carried out at pressures greater than atmospheric pressure.

According to the present invention, stage (a) and/or stage (b) may be carried out in the absence of heat transfer agents, for example by heating the reactant (II) under vacuum to dehydrate and/or pyrolyse said reactant (II).

Heat Transfer Agents

Preferably, both of stages (a) and (b) of the reaction are carried out in the presence of heat transfer agents. However stage (a) and/or stage (b) may be carried out in the absence of said agents.

At least one heat transfer agent is preferably used in the method of the present invention, in either stage (a), or in stage (b), or in both stage (a) i.e. azeotropic removal of water from the reactant (II), and stage (b), i.e. the pyrolysis of the dehydrated reactant (II). Mixtures of heat transfer agents, wherein each agent has the requisite properties may be used in each stage, or alternatively mixtures of heat transfer agents chosen so that the mixture has the requisite properties may be used. The reactant and/or reaction product is preferably insoluble or sparingly soluble even when heated in the heat transfer agent or mixture thereof used in each stage.

Any inert solvent for example aliphatic or aromatic hydrocarbons, or other polar aprotic solvents, having the properties here described are suitable for use as heat transfer agents.

Suitable heat transfer agents for use in the azeotropic removal of water in stage (a) include inert liquids which exhibit effective azeotropic properties with water and which are liquid at the reaction temperature. In particular aromatic hydrocarbons including for example toluene, xylene and cumene are suitable. Alternatively, straight or branched chained alkanes or cycloalkanes with the aforementioned boiling points and properties, such as octane, cycloheptane and cyclooctane may be used.

A different heat transfer agent may be used in stage (a) from the heat transfer agent used in stage (b).

Suitable heat transfer agents for use in stage (b) include inert materials which are liquid at the reaction temperature. Preferably these heat transfer agents are at least substantially water immiscible, although water miscible heat transfer agents may work under certain conditions, for example some water miscible glycols. Straight or branched chain alkanes, for example decane, dodecane and tetradecane have been found to be particularly effective. Furthermore, aromatic compounds such as phenyl ethers (for example diphenyl ether and propyl phenyl ether) having the above identified properties are also suitable for use.

Oily compounds, such as vegetable, hydrocarbon or silicone oils, or alternatively polyoxylene glycols and mixed polyoxylene glycols having the above properties may also be used.

The method may be carried out in the absence of heat transfer agents, in a suitable manner, e.g. in a fluidised bed reactor or oven.

Stage (a) of Method—Dehydration of Reactant

The reactant (II) and the heat transfer agent for use in the azeotropic removal of water may be charged to a suitable reaction vessel in any appropriate manner. The heat transfer agent for use in this stage is chosen in accordance with the properties required for said agent as described hereinabove.

The weight to volume ratio for the amount of reactant (II) to the amount of heat transfer agent is preferably within the range of 1:100 to 10:1, preferably 1:10 to 1:1.

The reaction mixture is typically heated to a temperature (dependent upon the heat transfer agent, employed, if any) sufficient to effect the azeotropic removal of water from the reaction (II). This temperature will usually be within the range of from 50° C. to 175° C., preferably 75° C. to 130° C. The azeotropic distillation is typically stopped when the temperature of the reaction mixture reaches a constant boiling point. For example, when using toluene as the heat transfer agent the reaction is stopped at a temperature within the range 108° C. to 113° C., most preferably within the range 110° C. to 112° C.

The azeotropic distillation is continued until substantially all the water of dehydration of the reactant (II) is removed. This is typically complete within 0.1 to 20 hours, for example 0.25 hours to 10 hours, such as 0.3 hours to 3 hours. The reaction mixture resulting from the completion of stage (a) is allowed to cool to between 25° C. to 60° C. prior to the second stage of the process of the invention. It may however, if circumstances permit, be possible to continue with said second stage before the reaction mixture has so cooled.

Stage (b) of Method—Pyrolysis of Dehydrated Reactant

Optionally, either before, during or after stage (b) at least one drying agent may be added to the reaction mixture. This addition of at least one drying agent aids the removal of any residual water from the reaction mixture. Preferably a relatively small amount of drying agent is added. Particularly preferred is the addition of at least one anhydride to the reaction mixture, preferably during the heating thereof in stage (b). Preferably the anhydride is acetic anhydride. It is preferred that the amount of said drying agents used is less than 70% by weight, based on the total amount of reactant (II), most preferably less than 60%, e.g. less than 55%.

Stage (b) involves the removal of the first heat transfer agent and the pyrolysis of the dehydrated reactant (II). The second heat transfer agent, chosen in accordance with the requisite properties mentioned hereinabove may be added by any suitable means and in any suitable manner to the reaction mixture obtained from the above first stage. It is particularly preferred that the second heat transfer agent, e.g. dodecane, or diphenylether is added to the reaction mixture at a temperature lower than the flash point of the second heat transfer agent. Typically the total amount of the second heat transfer agent is simply added to said reaction mixture in one addition. However, it is possible to add aliquots of said heat transfer agent if so required.

The weight to volume ratio for the amount of reactant (II) to the amount of heat transfer agent should be sufficient to maintain a stirrable slurry at the reaction temperature, with said ratio typically being within the range of 1:100 to 10:1, preferably 1:10 to 1:1.

The reaction mixture during stage (b) is preferably heated to a temperature within the range given below dependent upon the boiling point of the second heat transfer agent employed. However, in order to provide an alkene phosphonic acid product of high purity it is important to maintain the temperature below the decomposition temperature of said reactant or product. Preferably the reaction mixture is maintained at a temperature of from 170° C. to 300° C., most preferably 180° C. to 250° C., especially 190° C. to 240° C. The reaction time during stage (b) is obviously dependent upon the temperature used, but is usually in the range of from 1 hour to 15 hours, preferably 2 hours to 14 hours, most preferably 2.5 hours to 13 hours, after which time the reaction mixture is allowed to cool to between 25° C. and 60° C. At this stage the reaction mixture may comprise the alkene phosphonic acid or salt product and anhydrides thereof.

Water may be added to the reaction mixture, preferably in a quantity sufficient to dissolve the product and thus produce a discrete aqueous solution thereof.

The aqueous product-containing layer and the second stage heat transfer agent may be separated by means of one or more steps, preferably by any suitable technique, for example by using a separating funnel. Several separations may be required in order to remove as much of said heat transfer agent as possible from said aqueous layer.

Stage (c) of Method: Conversion of Anhydrides to Corresponding Acid or Salt

Stage (c), which is optional, involves the conversion of any anhydrides produced during stage (b) to their corresponding alkene phosphonic acids (I).

This stage may optionally be effected concurrently with the second stage (b), i.e. the conversion of anhydrides to the corresponding acid or salt may be effected in a simultaneous stage with the pyrolysis of the dehydrated reactant. This method of conversion is particularly preferred as products of very high purity may be obtained.

The aforementioned conversion may be achieved by the addition of at least one base to the reaction mixture of stage (b), either before or during that stage. Suitable bases include inorganic bases such as alkali and alkaline earth metal hydroxides, carbonates, bicarbonates and hydrides e.g. sodium hydroxide, sodium carbonate, sodium bicarbonate and sodium hydride. Also suitable are organic bases such as alkali metal and alkaline earth metal acetates, and alkoxides, for example sodium acetate, sodium methoxide and sodium ethoxide. Nitrogen-containing bases may also be used, for example trialkylamines. The base may be added as a solution, for example sodium methoxide in methanol.

It is preferred that the mole ratio of the base to the reactant (II) is in the range 6:1 to 1:6, such as 4:1 to 1:4, preferably 3:1 to 1:1, most preferably 3:1 to 2:1.

In addition to, or instead of, the above method involving the addition of a base, the conversion of the reaction mixture may be effected by heating an acidic or alkaline solution of the anhydride to convert any anhydrides to the corresponding acids or salts. This may be achieved, for example by heating said solution at a temperature of from 30° C. to 80° C., for 0.5 to 5 hours, e.g. 60° C. for 3 hours. A product of high purity is thus obtained.

The above conversion methods are preferred as they have been found to be particularly effective and to yield a product of very high purity. The method of conversion involving the addition of the base is particularly preferred.

Alternatively, any other process which facilitates the conversion of any anhydrides into alkene diphosphonic acids may be employed, for example the use of one or more catalysts e.g. diazabicycloundecane (DBU) in the base hydrolysis of said anhydrides.

Isolation and Purification

Where it is required to remove cations e.g. sodium or calcium, from the product the aqueous product containing solution may be subjected to an ion-exchange process, for example column chromatography using ion exchange resins.

Any other suitable, conventional purification process may alternatively be used.

The product may be isolated by any conventional technique, for example recrystallisation from a suitable solvent such as aqueous industrial methylated spirits (IMS). This may be achieved by adding IMS to a warmed aqueous solution of the product followed by cooling, and filtration to remove the product crystals. Alternatively the product may for example be isolated from the aqueous solution by rotary evaporation under reduced pressure for a suitable period of time.

The acid product may also for example, be isolated by the addition of a suitable mineral acid, e.g. $H_2SO_4$, in the presence of a suitable solvent, e.g. methanol and/or ethanol to the salt of the acid product followed by recrystallisation of the mineral acid salt from the solvent to yield said acid product.

The tetra sodium salt of the product is typically obtained as a white or off white crystalline solid. Yields of at least 80% are usually obtained with the process of the invention. The purity of said products is typically found to be at least 81 mol %, often at least 90 mol %.

Uses

The alkene phosphonic acids produced according to the method of the present invention, find particular use as chelants for metals e.g. calcium, and as intermediates for medically active components such as anti inflammatory and arthritic agents and other pharmaceutical uses. They also find use in heterocyclic synthesis. Because of the polymerisable nature of the alkene diphosphonic acids they also find application as co-monomers for polymeric compositions. In particular the products find use as co-monomers in polymeric compositions comprising unsaturated co-monomers including polymeric flame retardant compositions (see our co-pending published application EP-A-0780406). Also, said acids find use as ion exchangers for transuranics because of their chelancy effect.

The invention will be further described with reference to the following examples.

EXAMPLES

Example 1

The Single Stage Preparation of the Tetra-sodium Salt of VDPA From the Hexa-sodium Salt of ADPA Dimer

[Formula (II) wherein $R^1$ is $CH_3$,

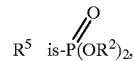

and $R^2$ is Na]

To toluene (400 ml), the hexa-sodium salt of aceto diphosphonic acid dimer (ADPA) (100 g, 0.13 moles) was added, and the reaction mixture heated to 106° C. to remove water azeotropically. The azeotropic distillation was stopped when the temperature reached 110.6° C., and the reaction mixture allowed to cool to ambient temperature. Solid sodium methoxide (20 g, 0.37 moles) and diphenylether (400 ml) were then added to the cooled reaction mixture, which was subsequently heated to, and maintained at, 216° C. for 3 hours. During heating, toluene was distilled out from the reaction mixture. After the heating, the mixture was allowed to cool.

Water (675 ml) was added to the cooled reaction mixture, and then the aqueous product containing solution separated from the diphenylether and then heated to 50° C. Industrial methylated spirits (180 g) was added to the aqueous solution which was then allowed to cool. The crystalline white solid reaction product was isolated by filtration.

The tetra-sodium salt of VDPA was produced in a yield of 79%. Analysis of the product by $^{31}P$ nmr determined the product to be of a very high purity (96 mol %).

Example 2

Multistage Preparation of the Tetra-sodium Salt of VDPA From Phosphorous Acid (i) First Stage: Preparation of the Hexa-sodium Salt of the ADPA Dimer (Intermediate)

Phosphorous acid (656 g, 8 moles) was added to acetic acid (1200 ml) in a reactor at room temperature. The reaction mixture was heated to 121° C. over 100 minutes, during which time acetic anhydride (900 g, 8.8 moles) was slowly added. After approximately 16 hours of a total time of 30 hours at 121° C., a white precipitate appeared in the reaction mixture. After this time the reaction mixture was cooled to 40° C. and then filtered.

Next, the filtered solid (900 g, 2.4 moles; which was still wet with acetic acid) and 50% w/w aqueous sodium hydroxide (1150 g) were added with stirring to water (2000 g), at a rate which maintained the temperature of the reaction mixture below 60° C. and the pH in the range 7–11.

The ADPA dimer product was precipitated from the reaction mixture, filtered, washed with cold alkaline water having a pH of approximately 11.5 and dried to constant weight in vacuo (1500 g, 65% yield). $^{31}P$ nmr showed no observable phosphorus containing impurities in the product. The product contained 14 $H_2O$ molecules as water of crystallisation.

(ii) Second Stage: Preparation of Tetra-sodium Salt of VDPA From the Hexa-sodium Salt of ADPA Dimer To toluene (800 ml), the hexa-sodium salt of ADPA dimer from the first stage (400 g, 0.53 moles) was added to the mixture heated to, and maintained at, a temperature of 106° C. for 3 hours during which time water (130 ml) was removed azeotropically. The reaction mixture was cooled to 60° C. and dodecane (800 ml) added, after which the temperature was raised to, and maintained at, 200° C. to 206° C. for 11½ hours. Toluene (350 ml) was removed from the reaction mixture during the heating of the reaction mixture up to the final temperature.

The reaction mixture was then cooled and water (800 ml) added. The solid reaction product dissolved, and the product-containing aqueous layer was separated from the dodecane in a separating funnel.

The separated aqueous layer (approximately 300 ml) was passed over an ion-exchange resin, and reduced on a rotatory evaporator at 40° C. for approximately 4 hours.

The VDPA was produced in a yield of 64%. Analysis of the final solution by $^-P$ nmr determined the product to be of high purity (81 mol %).

Example 3

Preparation of the Tetra-sodium Salt of VDPA From the Hexa-sodium Salt of ADPA Dimer To a sample of the recrystallised hexa-sodium salt of ADPA dimer of Example 2 Stage (i) (10 g, 0.013 moles), toluene (150 ml) was added. The mixture was brought to, and maintained at 106° C. for approximately 30 minutes. At the end of this time approximately 2 ml of water had been removed azeotropically from the reaction mixture, which was then cooled to 60° C. Dodecane (150 ml,) was added to the cooled reaction mixture, and the temperature then raised to 214° C. in order to remove the toluene. The reaction mixture was maintained at approximately 214° C. for a further 8 hours after which time the mixture was cooled and water (50 ml) added. The solid product dissolved upon addition of the water, and the aqueous product-containing layer was separated from the dodecane. Purification of the tetra-sodium salt of VDPA was undertaken as described in Example 2.

Analysis of the tetra-sodium VDPA product by $^{31}P$ nmr determined the product to be of high purity (87.5 mol %).

Example 4

Preparation of Tetra-sodium VDPA From the Hexa-sodium Salt of ADPA Dimer

To toluene (150 ml), the hexa-sodium salt of ADPA dimer (20 g, 0.026 moles) was added and the reaction mixture subsequently heated to, and maintained at 106° C. for 1 hour during which time water (6 ml) was removed. The reaction mixture was cooled to 60° C. and dodecane (150 ml) added. Acetic anhydride (10 g) was added shortly after heating of the reaction mixture had commenced, to remove further traces of water with the temperature being raised to 214° C.

to remove the toluene and acetic acid. The heating was continued for approximately 8 hours, after which time the mixture was cooled to 60° C. and water (150 mls) added. The solid reaction product then dissolved, and the aqueous product-containing layer was separated from the dodecane. Purification of the reaction product was undertaken as described in Example 2.

Analysis of the final solution of tetra-sodium salt of VDPA by $^{31}$P nmr determined the product to be of high purity (84 mol %).

Example 5

Preparation of Tetra-sodium VDPA From Hexa-sodium salt of ADPA Dimer

To toluene (800 ml), the hexa-sodium salt of ADPA dimer (200 g, 0.26 moles) was added and the reaction mixture heated to 106° C., at which it was maintained for 3 hours to allow for the azeotropic removal of water (approximately 125 ml). The reaction mixture was then cooled, and dodecane (80 ml) added, after which the temperature was raised to, and maintained at, 214° C. for 8 hours to remove toluene. After this time the mixture was cooled to 60° C. and water added (80 ml). The solid reaction product dissolved and the aqueous product-containing layer was separated from the dodecane. Purification of the reaction product was undertaken as described in Example 2.

Analysis of the product by $^{31}$P nmr determined the product to be of high purity (81 mol %).

Example 6

Multistage Preparation of the Tetra-sodium Salt VDPA From ADPA Dimer Precursor (i) First Stage: Preparation of the Hexa-sodium Salt of the ADPA Dimer (Intermediate)

ADPA precursor (621 g, 1.6 moles; the precursor containing some acetic acid) and acetic acid (503 g 8.4 moles) were added to a flask, heated to, and maintained at approximately 120° C. for 35 hours. Diphenylether (400 ml) was then added, and the reaction mixture heated to 120° C.–130° C., with acetic acid being removed by distillation. The reaction mixture was then added to water (500 ml) concurrently with a 50% w/w aqueous solution of sodium hydroxide (700 g), at a rate so as to maintain the temperature at below 60° C. and the pH between 7 and 11. The hexa-sodium salt of ADPA dimer was precipitated, filtered, washed with alkaline water (approximately 2000 g, pH 11.5) and dried to constant weight in a vacuum oven.

The sodium salt of ADPA dimer was obtained in an amount of 436 g (yield 73%).

(ii) Second Stage: Preparation of the Tetra-sodium Salt of VDPA From the Hexa-sodium Salt of ADPA Dimer To toluene (800 mls) was added the hexa-sodium salt of ADPA dimer from the first stage (400 g, 0.525 moles), and the reaction mixture heated to 106° C. Water was removed azeotropically until the temperature reached 110.6° C. The reaction mixture was cooled to 60° C. and a solution of 25% w/w sodium methoxide in methanol (384 g) was added. The temperature of the reaction mixture was increased gently to allow for the removal of methanol by distillation and when all the methanol had been removed the reaction mixture was allowed to cool to 60° C. Diphenylether (800 ml) was then added. The temperature was increased to, and maintained at 216° C. for 3 hours, with toluene being removed from the reaction mixture as the temperature was increased. The reaction mixture was then again allowed to cool.

To the cooled reaction mixture, water (2500 ml) was added and the diphenylether separated off. The aqueous product-containing solution was heated to 50° C. and industrial methylated spirits (640 g) added. The solution was allowed to cool to 60° C. to recrystallise the product which was filtered and dried to constant weight in a vacuum oven.

The tetra-sodium salt of VDPA was produced in an amount of 316 g (62% yield). Analysis of the product by $^{31}$P nmr determined the product to be of very high purity 95.5 mol %.

Example 7

Preparation of Vinylidene Diphosphonic Acid, Tetra-sodium Salt (VDPANa$_4$) by Thermolysis of ADPA Dimer, Hexa-sodium Salt (Dodecahydrate).

1000 g of hydrated ADPA dimer (1.38 moles) was heated at 200° C. in a fan assisted oven for 20 hours, to leave 700 g of a colourless, hygroscopic solid which was then cooled and dissolved in 2000 g water.

To this solution was added 234 g of 47% w/w sodium hydroxide. This mixture was heated to reflux (103° C.) for 5 hours.

After this time, 300 g of IMS was added to the refluxing solution over a period of 45 minutes, during which time the reflux temperature dropped to 83° C.

Cooling of the solution was continued to 30° C. over a period of 3 hours, during which time solids crystallised from solution. Filtration and air drying gave 945 g of a colourless solid which had a purity of 91.5% VDPANa$_4$ by $^{31}$P-NMR spectroscopy.

Thermogravimetric analysis of the hydrated solid showed a total water content of 42% by weight, indicating a chemical yield of 72% VDPANa$_4$ (548 g=1.99 moles) based on the starting ADPA dimer used.

What is claimed is:

1. A method of preparing a compound of formula (I): formula (I)

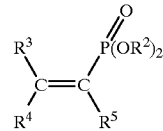

wherein:
each $R^2$ is independently selected from the group consisting of hydrogen, alkyl groups, alkali metals, alkaline earth metals and nitrogen-containing groups;
$R^3$ and $R^4$ are independently selected from the group consisting of hydrogen and alkyl groups;
$R^5$ is selected from the group consisting of hydrogen, alkyl groups and

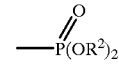

wherein said method comprises the steps of:
(a) azeotropically removing water from a reactant of formula (II):

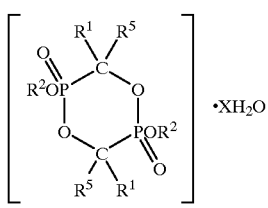

formula (II)

wherein: $R^1$ is $CHR^3R^4$; $R^2$, $R^3$, $R^4$ and $R^5$ are as defined above; and X is a number between 0 and 20; to form a dehydrated reactant (II);

(b) pyrolysing said dehydrated reactant (II) at a temperature of from 170° C. to 300° C., and thereafter (c) optionally, converting any anhydrides formed by the pyrolysing step (b) to the corresponding acid or salt having the formula (I).

2. The method of claim 1, wherein (a) said azeotropic removal of water from said reactant (II) is carried out by dehydrating a reactant of formula (II) in the presence of at least one inert liquid heat transfer agent which exhibits effective azeotropic properties with water and which is liquid at the reaction temperature; and (b) said pyrolysis of dehydrated reactant (II) is carried out by adding said at least one inert heat transfer agent to the reaction mixture from (a), and maintaining said reaction mixture at 170° C. to 300° C. until pyrolysis of said dehydrated reactant (II) is complete.

3. The method of claim 1, wherein said pyrolysis of said dehydrated reactant (II) is carried out in the presence of at least one base, and optionally also at least one inert heat transfer agent.

4. The method of claim 1, wherein each of said groups $R^2$, $R^3$ and $R^5$ is a $C_1$–$C_6$ alkyl group.

5. The method of claim 1, wherein said group $R^2$ is an amine salt.

6. The method of claim 1, wherein at least one of said steps (a), (b) and (c) is carried out under a pressure less than atmospheric pressure.

7. The method of claim 1, wherein at least one of said steps (a), (b) and (c) is carried out at a pressure greater than atmospheric pressure.

8. The method of claim 2, wherein said at least one heat transfer agent is an inert liquid selected from the group consisting of aliphatic hydrocarbons, aromatic hydrocarbons and polar aprotic solvents.

9. The method of claim 2, wherein a different heat transfer agent is used in step (a) from the heat transfer agent used in said step (b).

10. The method of claim 2, wherein the weight to volume ratio for the amount of said reactant (II) to the amount of said at least one heat transfer agent is within the range 1:100 to 10:1.

11. The method of claim 10, wherein said ratio is within the range 1:10 to 1:1.

12. The method of claim 1, wherein said step (a) is carried out at a temperature within the range 50° C. to 175° C.

13. The method of claim 12, wherein said temperature is within the range 75° C. to 130° C.

14. The method of claim 2, wherein said at least one heat transfer agent consists essentially of toluene and said reaction is stopped at a temperature within the range 108° C. to 113° C.

15. The method of claim 1, wherein the reaction mixture resulting from completion of said step (a) is cooled to between 25° C. to 60° C. prior to said step (b).

16. The method of claim 1, wherein at least one drying agent is added to said reaction mixture, said at least one drying agent comprising at least one carboxylic acid anhydride.

17. The method of claim 16, wherein said at least one drying agent is added either:
i) before said step (b);
ii) during said step (b); or
iii) after said step (b).

18. The method of claim 16, wherein the amount of said at least one drying agent used is less than 70% by weight based on the total amount of said reactant (II).

19. The method of claim 1, wherein said reaction mixture during said step (b) is maintained at a temperature of from 170° C. to 300° C.

20. The method of claim 19, wherein said temperature is in the range of 180° C. to 250° C.

21. The method of claim 1, wherein after the completion of said step (b) the reaction mixture is cooled to between 25° C. and 60° C.

22. The method of claim 2, wherein sufficient water is added to the reaction mixture, after the completion of said step (b), to produce a discrete aqueous product-containing layer, said layer being separable from said at least one heat transfer agent.

23. The method of claim 1, wherein at least one base is added to the reaction mixture of step (b), either before or during step (b).

24. The method of claim 23, wherein said at least one base is an inorganic base selected from the group consisting of sodium hydroxide, sodium carbonate, sodium bicarbonate and sodium hydride.

25. The method of claim 23, wherein said at least one base is an organic base selected from the group consisting of alkali metal acetates, alkaline earth metal acetates and alkali metal alkoxides.

26. The method of claim 23, wherein the mole ratio of said at least one base to said reactant (II) is in the range 6:1 to 1:6.

27. The method of claim 1, wherein said conversion of said reaction mixture from anhydride to said product having the formula (I) is effected by heating an acidic or alkaline solution of said anhydride at a temperature from 30° C. to 80° C. for 0.5 hours to 5 hours.

28. The method of claim 27, wherein said conversion of anhydride is accelerated by means of at least one catalyst.

29. The method of claim 28, wherein said at least one catalyst comprises diazabicycloundecane (DBU).

30. The method of claim 22, wherein said aqueous product-containing layer is subjected to an ion-exchange process.

* * * * *